United States Patent [19]

Devos et al.

[11] 4,163,691

[45] Aug. 7, 1979

[54] INSOLUBLE ENZYMATICALLY ACTIVE PARTICLES

[75] Inventors: Francis Devos; Patrick Leroy; Michel Huchette, all of Lestrem, France

[73] Assignee: Roquette Freres, Lestrem, France

[21] Appl. No.: 803,244

[22] Filed: Jun. 3, 1977

[30] Foreign Application Priority Data

Jun. 4, 1976 [FR] France .................... 76 17155

[51] Int. Cl.$^2$ ................ C07G 7/02; C12K 1/00
[52] U.S. Cl. ................................... 435/174
[58] Field of Search ............ 195/54, 59, 63, 68, 195/DIG. 11, 56, 31 F

[56] References Cited

U.S. PATENT DOCUMENTS

| 3,838,007 | 9/1974 | van Velzen | 195/68 X |
| 3,972,776 | 8/1976 | Vieth et al. | 195/59 X |
| 3,980,521 | 9/1976 | Amotz et al. | 195/31 F |
| 3,989,597 | 11/1976 | Lee et al. | 195/59 X |

FOREIGN PATENT DOCUMENTS 1257263 12/1971 United Kingdom .

*Primary Examiner*—David M. Naff
*Attorney, Agent, or Firm*—Larson, Taylor and Hinds

[57] ABSTRACT

Insoluble enzymatically active particles are produced by forming an intimate mixture of a jellifying protein such as gelatin and microbial cells containing an enzyme such as glucose isomerase, passing the mixture through a die to produce threads, passing the threads into cold water to jellify the threads, contacting the jellified threads with a crosslinking agent and cutting the resultant crosslinked threads into pieces.

9 Claims, 1 Drawing Figure

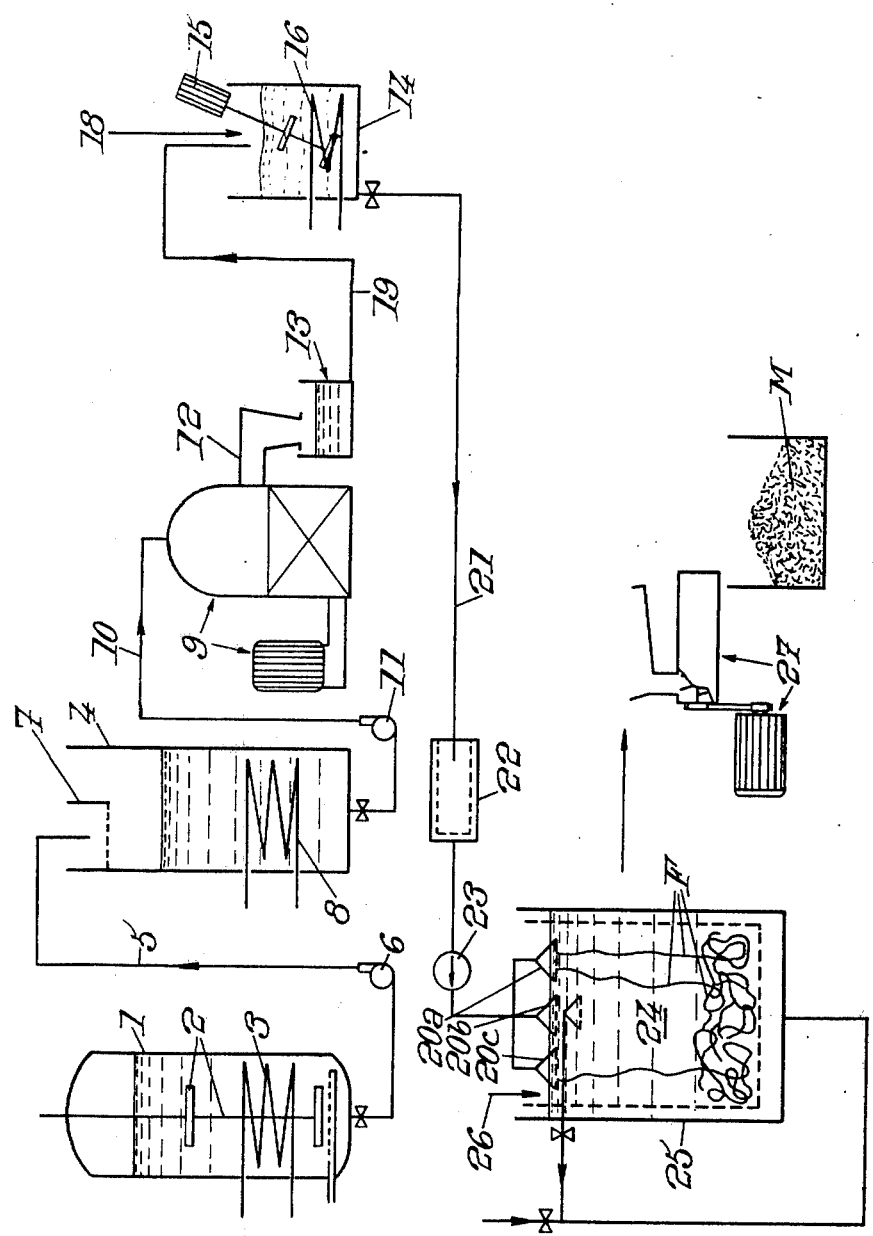

INSOLUBLE ENZYMATICALLY ACTIVE PARTICLES

The invention relates to a process for manufacturing insoluble enzymatically active particles. More particularly it relates to the manufacture of particles of this type which are useful for filling columns, beds and other reaction vessels in which said particles are placed in contact with the medium on which their enzymatic activity must be exerted.

The invention also relates, to novel industrial products, comprised of insoluble enzymatically active particles produced by the application of the process according to the invention. This process is characterised by the following successive steps:

Constituting an intimate mixture of an endocellular enzyme, in the form of a slurry of microbial cells, and a jelling or jellifying protein, notably gelatin, jellifying the protein of this mixture by introducing the mixture into cold water, before or after division of said mixture, the divided jellified protein mixture being kept for a sufficient time in contact with an effective amount of a cross-linking agent for the jelling protein.

According to a preferred embodiment of the aforementioned process, the mixture of gelatin and the slurry of microbial cells is divided into threads by passage through a die and introduced into ice-water, the skein of threads thus produced being kept for a sufficient period in contact with an effective amount of glutaraldehyde, then cut up into pieces of such a length that, taking into account the diameter of the threads, no clogging phenomenon is produced at the time of their use. According to a preferred embodiment, the aforementioned process is applied to the manufacture of insoluble particles of endocellular glucose-isomerase and gelatin.

The novel industrial product according to the invention is characterised by the fact that it is comprised of a mass of pieces of thread in the shape of "vermicelli" having an average length longer than 0.2 mm, generally less than 10 mm and, preferably, close to 1 mm and a diameter of 0.2 to 5 mm, constituted by an intimate mixture of enzyme, notably of endocellular glucose-isomerase, and of gelatin cross-linked by a bridging agent.

Apart from the above-said features, the invention comprises still other features which are preferably used at the same time and which will be more explicitly described below. The invention will in any case be better understood by virtue of the further description which follows and the accompanying drawing, which description and drawing are given with reference to preferred embodiments.

The single FIGURE of this drawing is a diagrammatic view showing the principal elements of an embodiment of an installation for the application of the process according to the invention.

In order to manufacture insoluble enzymatically active particles of the type concerned, according to the invention, the following procedure or an equivalent is followed:

Firstly, an endocellular enzyme is prepared in the form of a slurry of microbial cells. To do this, the procedure used may be as is described below:

In manner known in itself, the selected microbial strain is cultivated so as to prepare a culture wort. Since the particles resulting from the process according to the invention, have to possess the highest possible enzymatic activity, a slurry with a dry material content as high as possible should be isolated from the culture wort. To do this, it is possible to resort to centrifugation and in order to improve the disposition of the wort as much as possible to centrifugation, it is subjected to a moderate heat treatment at a temperature of less than about 55° C. Before the heat treatment, however, the culture wort or must is sifted to remove coarse insoluble particles. Centrifugation of the sifted wort is carried out so that a slurry is obtained having a dry matter content of at least the order of 10%, generally about 14%. The resulting slurry which constitutes the raw material for the process according to the invention is, according to this process, successively subjected to the following operational steps:

The slurry is first mixed intimately with a jellifying protein, preferably a jellifying protein comprised of gelatin. The proportion of gelatin with respect to the amount of slurry is from 3 to 20% by weight, preferably on the order of 10% by weight, the gelatin being in powder form. To have a good dispersion of the jellifying protein, notably gelatin, the temperature of the slurry is kept at the temperature of less than about 55° C. during the addition of the gelatin powder which is done with vigorous stirring. At the same time as the gelatin is added, there is preferably added an effective amount of an enzyme stabilising agent. The proportion of stabilising agent which can be selected from the group comprising magnesium and cobalt salts, notably magnesium chloride and sulfate, is generally on the order of 1 per 100 with respect to the mass of slurry.

The constituent protein of the intimate mixture thus produced according to the invention, is then jellified, after or before division of said mixture, by introduction into cold water. The division of the mixture is carried out advantageously by passing the latter through a die immersed in cold water so that the threads emerging from the die are in the midst of said water. The skein of threads obtained is kept in contact with an effective amount of a cross-linking agent for a sufficient period. Before passing through the die, the above-said mixture is, preferably, sieved to remove insoluble particles, possibly introduced by the gelatin.

For the passage through the die which is advantageously selected so that the threads obtained have a diameter of the order of 0.2 ot 5 mm, the above-said mixture is subjected to sufficient pressure so that passage is effected uniformly through all the die orifices but at not too high a pressure to avoid dispersion in the cold water. Experimentation has shown that a pressure of the order of 0.2 kg/cm2 is suitable. The temperature of the iced water into which the threads emerging from the die penetrate may be from about 1° to 2° C. The sudden cooling of the threads due to the immersion in iced water results in the gelatin congealing in the mass of microbial cells. During the whole period of spinning, a slight rising flow of iced water is advantageously maintained, to limit felting of the threads.

It may be used to renew the water in which the threads are collected; this water contains a proportion of enzyme stabiliser similar to the proportion of stabiliser present in the above-said mixture. The agent for cross-linking the jellifying protein, which is preferably glutaraldehyde, may be present in the ice water into which the above-said threads are led. It can also be added only when all the mixture has been spun.

The proportion of cross-linking agent, with respect to the starting mass of slurry is on the order of 0.5 to 5%, generally about 2%.

It may be applied in the form of a 50% technical solution in water.

The contact between the thread and the solution of crosslinking agent is maintained, preferably with a rising flow of water for a sufficient period to completely insolubilise the gelatin present by cross-linking. In general, the period of contact is from 10 to 15 hours.

The skein of threads is then washed to remove the traces of cross-linking agent which have not reacted, then cut up so as to obtain pieces of thread of a length such that, taking into account the diameter of these threads, no clogging phenomenom is produced at the time of application. Experience has shown that good results are obtained with pieces of thread of a length greater than 0.2 mm, less than 10 mm, and preferably, in the vicinity of 1 mm.

The mass of cut threads in the form of vermicelli, which can be applied as such after removal of fine particles by sifting, or stored after drying, constitutes a novel industrial produt. This mass can be wrung to a dry matter content of 23 to 25%. For storage, it can be dried, for example in a fluidised bed at 60° C., to a dry material content higher than 90%. The process according to the invention may be practiced in an installation of the type shown in the single diagrammatic figure of the drawing which comprises:

a fermentation vessel 1 in which the selected microorganism is cultivated, this vessel being provided with a stirring system 2 and a heating system 3;

a storage vat 4 for the culture must or wort at which the wort arrives through a pipe 5 provided with a pump 6 and at the inlet of which a sifting device 7 is provided, this vat including also a heating system 8 to apply any heat treatment to the must;

a centrifugation chamber shown generally at 9 at which the wort arrives through a pipe 10 provided with a pump 11 and from which the slurries emerge through a pipe 12;

a storage vat 13 for the slurries and a vat 14 provided with a stirring system 15 and with a heating system 16 and in which the slurries are mixed with the jellifying protein and the stabilising agent introduced along the arrow 18, the vat 14 being connected to the vat 13 by a pipe 19;

a system of dies 20a, 20b, 20c, . . . at which the mixture arrives through a pipe 21 in which a sieve 22 is provided and a volumetric pump 23, said dies being arranged so as to open under the surface of a volume of ice water 24 contained in a tank 25 into which is led along the arrows 26, a cross-linking agent and a stabilising agent for the protein, the tank 25 being provided with a system (not shown) enabling a rising flow of water to be maintained;

a device generally denoted by 27 and adapted to ensure the cutting up of the skeins of threads F recovered from the tank 25 and opening into a storage tank for the cut threads, constituting a mass M of pieces of thread, that is to say the industrial product according to the invention.

To illustrate the process according to the invention, it is described below applied to a particular microorganism, namely Streptomyces violaceoniger, more particularly the strain CBS No. 409-73 of this microorganism, deposited by the Company Roquette Frères (in this respect see French Pat. No. 2,225,514), this microorganism being a producer of endocellular glucoseisomerase.

Starting from a culture of Streptomyces violaceoniger, strain CBS No. 409-73, introduced into a fermenter of 30 m$^3$ according to the process described in the above-said French Pat. No. 2,225,514, 6 m of culture must are taken off. This culture must is sieved on a rotary seive of the "LARSSON" type, for example that which is marketed by the Company ALFA-LAVAL, lined with a stainless steel gauze of mesh size 200 microns. It is then heated to 55° C. and centrifuged in a selfcleaning centrifuge of the WESTFALIA SAMR 15 037 type at a flowrate of 3 m$^3$/hour. Partial washing for 1.4 seconds every 2 minutes 30 seconds is provided. In one hour of centrifugation, 200 liters of slurry are collected with a dry matter content of 14% and having an enzymatic activity of 1600 units per gram of slurry, namely 1600 mg of levulose formed in one hour starting from a 10% dextrose solution, at a temperature of 70° C. and a pH of 8.5. These slurries are collected in a tank of 250 liters provided with a stirrer of the type marketed by the RAYNERI Company with an installed power of 3 HP. The tank is also provided with a heating coil with a flow of hot water keeping the slurries at 55° C.

To these slurries, there is added, with vigorous stirring and at 55° C., 20 kg of powdered gelatin, namely 10% of gelatin calculated with respect to the volume of slurry (gelatine of grade corresponding to 220 BLOOM units) and 200 grams of magnesium chloride as an enzyme stabiliser.

After a last sifting through a sieve with a mesh size of 200 microns, the suspension thus prepared is injected through a die into a water tank of 800 liters cooled to 1-2° C. For the injection a volumetric pump of the F 2 M type marketed by the P.C.M. Company, under MOINEAU license, is used. The die used is a plate of stainless steel of 10 cm diameter, perforated with 400 holes of 500 microns diameter; the injection flowrate is 70 liters/hour, the service pressure being 0.2 kg/cm$^2$. On emerging from the die, and on entry of the threads formed into the ice water, the gelatin is congealed in the mass of Streptomyces cells. During the whole time of spinning, a slight rising flow of cold water is maintained to avoid too much felting of the threads produced. After 3 hours spinning, any enzyme imprisioned in the gelatin is in the tank. In about a half hour the water in which the threads are collected is renewed; the water used throughout the process is softened water containing 1.0 gram of magnesium chloride per liter.

For cross-linking the gelatin, there is added 8 kg of a technical solution of 50% glutaraldehyde, namely an equivalent of 2% of glutaradehyde calculated on the volume of slurry. Contact is then maintained for 15 hours at a temperature of 2° C. and the gradual disappearance of the reactant is measured. A slight flow is maintained throughout the process to render all of the enzymatic preparation accessible to the cross-linking agent.

Once the cross-linking has been completed and after washing to remove traces of free glutaraldehyde, the skeins are cut up through a rotary knife device of the type marketed by the HOBART Company and equipped with a 4 mm grid, which results in "vermicelli" of an average length equal to 4 mm. Due to this cutting up, the filling coefficient in the columns is improved.

The cut up granules are usable as such for continuous isomerisation, their activity brought to the gram of drained moist granule being from 600 to 700 units/gram, the content of dry matter being 23-25%. Drying of these granules in a fluidised bed at 60° C. follows, which gives, after 2 hours, granules whose content of dry matter is greater than 90% and whose average activity is 2700 units/gram/sec. The product thus obtained can be applied to the continuous isomerisation of glucose. To do this, it is possible to proceed as follows:

4 isomerisation columns of a diameter of 25 cm and 200 cm in height are constructed. These columns are provided with a bottom gauze of 0.5 mm mesh width. On this gauze and in the water, 4 liters of calibrated gravel of 1 mm average diameter is added. Then watching that the addition is done under a level of water to avoid including air, 70 kg of moist vermicelli is added, which represents about 94 liters of vermicelli.

In these columns is percolated a starch hydrolysate with 94% true dextrose containing 5 to 6% of polyholosides, its absolute rotary power being about +56°, its content of dry matter 42% and its temperature 64°-65° C. The pH of the hydrolysate is adjusted with sodium carbonate to a value of 8.5.

Under these conditions, it was possible to achieve isomerisation of the starch hydrolsate to 42% fructose in 4 weeks.

The average weekly flow rates were:
80 liters/h—1st week
60 liters/h—2nd week
40 liters/h—3rd week
20 liters/h—4th week namely an average hourly flow rate of 50 liters/h for 4 weeks.

The total volume of treated solution is 35,000 liters per column. The pressure drop under these conditions never exceeded 0.5 kg/cm$^2$.

There were hence treated in this manner:

$(35,000 \times 1.1 \times 42)/100 = 16,170$ kg of dry hydrolysate.

This result was obtained from 70 kg of moist granules with 23% of dry matter or $70 \times 23/100 = 16.1$ kg of dry granules.

This result gives a ratio fo 1000 kg of dry hydrolysate isomerised to 42% fructose for 1 kg of dry enzyme.

As a result, and whatever the embodiment adopted, there is obtained, by means of the process according to the invention, particles of the type concerned which, have the highest possible enzymatic activity, the dilution of the cells in the jelling protein being the lowest possible, are insoluble in the reaction medium under the conditions of use (temperature, pH, pressure), are mechanically strong, that is to say do not give rise to crumbling during handling, changing of the columns, or in the course of treatments to avoid clogging, have a suitable size, a compromise between the highest possible apparent enzymatic activity and the hydrodynamic properties of reactors charged with these particles, are resistant to temperature.

As is self-evident and as emerges besides already from the foregoing, the invention is in no way limited to the embodiments and modes of application which have been more especially contemplated; it encompasses, on the contrary, all modifications.

We claim:

1. A process for manufacturing insoluble enzymatically active particles comprising, successively:
    forming an intimate mixture of a slurry of microbial cells containing glucose-isomerase as an endocellular enzyme at a temperature of less than about 55° C. and 3 to 20% by weight of gelatin as a jellifying agent,
    dividing the intimate mixture thus obtained into threads by passing said mixture through a die and into cold water to jellify said threads, said die being selected so that the threads obtained have a diameter of about 0.2 to 5 mm,
    contacting said jellified threads with 0.5 to 5% by weight of a cross-linking agent for said gelatin, based on the starting mass of the slurry, to provide cross-linking thereof, and then
    cutting said cross-linked threads into pieces having a length greater than 0.2 mm and less than 10 mm.

2. Process for manufacturing insoluble enzymatically active particles according to claim 1, wherein to the intimate mixture of endocellular enzyme and gelatin is added an enzyme stabilising agent.

3. Process for manufacturing insoluble enzymatically active particles according to claim 2, wherein the enzyme stabilising agent is selected from magnesium and cobalt salts.

4. The insoluble enzymatically active particles produced by the process of claim 1.

5. Process for manufacturing insoluble enzymatically active particles according to claim 1 wherein the slurry is of Streptomyces cells and has a dry material content of at least 10%, the crosslinking agent is glutaraldehyde and the contacting with said glutaraldehyde is for 10-15 hours.

6. Process for manufacturing insoluble enzymatically active particles according to claim 5, wherein said cells are Streptomyces violaceoniger cells.

7. Process for manufacturing insoluble enzymatically active particles according to claim 6, wherein the content of dry material of the slurry of Streptomyces violaceoniger cells is about 14% by weight, the amount of gelatin entering into the constitution of the intimate mixture about 10% by weight, the amount of glutaraldehyde about 2% by weight, the diameter of the threads about 0.5 mm and the length of the pieces of thread after cutting up about 1 mm on the average.

8. Process for manufacturing insoluble enzymatically active particles according to claim 5, wherein the glutaraldehyde is present in the cold water and the die is immersed in the cold water.

9. Process for manufacturing insoluble enzymatically active particles according to claim 8 wherein a rising flow of said water is maintained.

* * * * *